United States Patent [19]

Shimenkov

[11] 4,305,707
[45] Dec. 15, 1981

[54] MATRIX DEVICE FOR MAKING FILLINGS

[76] Inventor: Marat Shimenkov, 65-40 Parsons Blvd., #2A, Flushing, N.Y. 11365

[21] Appl. No.: 109,675

[22] Filed: Jan. 4, 1980

[51] Int. Cl.³ .............................................. A61C 9/00
[52] U.S. Cl. .................................................. 433/40
[58] Field of Search ........................ 433/40, 148, 149

[56] References Cited

U.S. PATENT DOCUMENTS 3,193,094 7/1965 Schulsted .......................... 433/149
3,473,226 10/1969 Arlers et al. ...................... 433/149

FOREIGN PATENT DOCUMENTS 2147905 6/1972 Fed. Rep. of Germany ........ 433/40

Primary Examiner—Robert Peshock
Attorney, Agent, or Firm—Ilya Zborovsky

[57] ABSTRACT

A device for making filling in posterior teeth has an elastic band member with two first portions and two second portions, and a wedge-shaped member insertable into the interior of the band member between the latter and a tooth so as to tighten the band member which is thereby retained on and abuts against a lateral surface of the tooth. The wedge-shaped member may be connected and formed of one piece with the band member. The band member may have a profiled lateral portion which is bendable and can abuts against the occlusal surface of the filling so as to compress and condense the filling material and to provide a required shape of the occlusal surface.

8 Claims, 1 Drawing Figure

U.S. Patent     Dec. 15, 1981     4,305,707
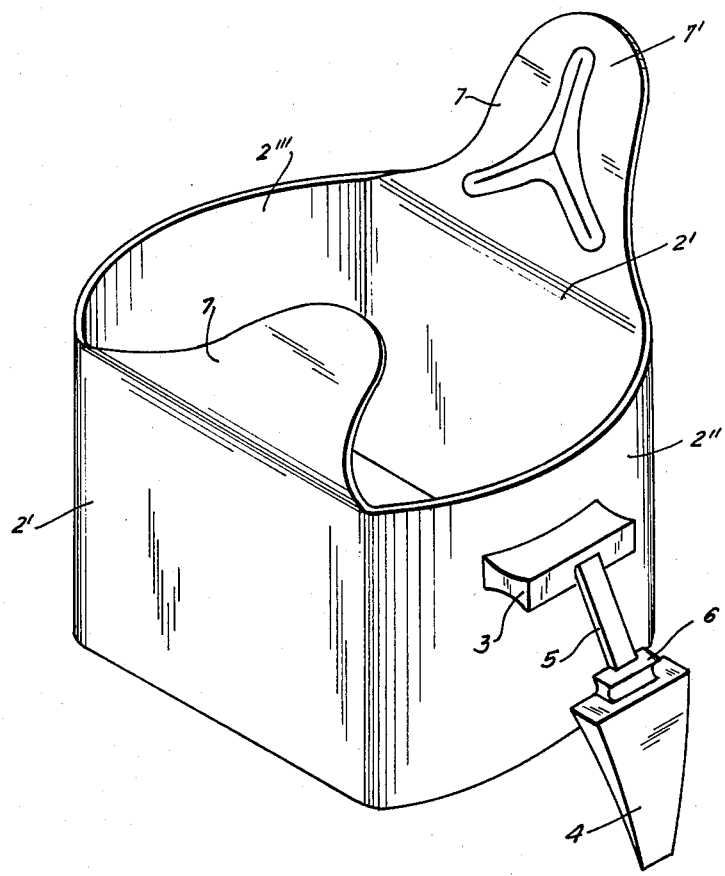

MATRIX DEVICE FOR MAKING FILLINGS

BACKGROUND OF THE INVENTION

The present invention relates to a matrix device for making fillings in posterior teeth.

Matrix devices for making fillings in posterior teeth are known in the art. A known matrix device includes a straight steel matrix band and a retainer of a Tofflemire type. The straight matrix band is put onto the tooth to be provided with a filling and tightened by a retainer which is located outside of the band and the tooth. Such a construction possesses the following disadvantages. The device includes two separate elements, namely the band and the retainer of a complicated construction. It is almost impossible to make fillings simultaneously in several neighboring teeth since several retainers must be utilized which interfere with one another. The retainer occupies a considerable space in the mouth which is very inconvenient for a dentist and a patient. It is especially inconvenient to make fillings in third molar tooth of both jaws wherein there is no space for the retainer. The device cannot be utilized for making fillings on lingual surface of the tooth. Finally, the tightening of the band by the retainer takes considerable time.

Another device is disclosed in the "Art and Science of Operative Dentistry", Sturdevant et al, FIGS. 10-27. This device includes a deformable band which is fitted onto a tooth and then its portion is squeezed by pliers so as to firmly embrace the tooth. An additional blade is placed between the tooth and the band, and is then removed after wedging. This construction has the following disadvantages. It requires the step of squeezing for reducing the diameter of the band, which step is time-consuming. Additional pliers is required, and it is very inconvenient to manipulate in the region of molar teeth with pliers. An additional blade is necessary during the process of making fillings.

A further device (FIGS. 10-39) includes a straight band which is cut, fitted onto a tooth, squeezed and then welded on the tooth close to the bends made by pliers. The excess band material is removed by scissors and the cut edge is folded. This device requires a lot of additional tool and welding equipment. The process of fitting the band is very inconvenient and time-consuming.

SUMMARY OF THE INVENTION

Accordingly, it is an object of the present invention to provide a matrix device for making fillings in posterior teeth, which avoids the disadvantages of the prior art.

More particularly, it is an object of the present invention to provide a matrix device for making fillings in posterior teeth, which has a simple construction, is easy to manufacture, occupies a small space in a mouth, is convenient to manipulate, and can be rapidly fit onto a tooth.

In keeping with these objects and with others which will become apparent hereinafter, one feature of the present invention resides, briefly stated, in a matrix device which has an elastic band with two first and two second sides forming a circumferentially closed contour, and a wedge-shaped tightening member arranged to be inserted between the band member and the tooth, inside the band member, so that it tightens the latter. Thereby, the band member firmly abuts against and is retained on the tooth under the action of this tightening.

When the device is designed in accordance with the present invention, it has a simple construction and is easy to manufacture. Several fillings may be simultaneously made in several neighboring teeth since no plurality of retainers is required. The matrix device occupies a very small space in the mouth and therefore is very convenient both for a dentist and a patient. Third molar teeth of both jaws can be easily provided with fillings with the utilization of the inventive device. Also fillings on the buccal surface of the teeth can be made, not only on the proximal surfaces of the latter. The tightening of the band member by the wedge-shaped member takes extremely little time.

In accordance with another feature of the present invention, a projection with a curved wall may be provided so that the band member may be engaged and held by a tool to be installed onto a tooth. A wedge-shaped member may be of one piece with the band member and connected to the above-mentioned projection by an elastic filament. The wedge-shaped member may have a portion with a curved wall so as to be readily grasped by the tool for insertion purposes.

In accordance with a further advantageous feature of the present invention, the band member may have a portion which is bendable between a distal position remote from the occlusal surface of the tooth, and a proximal position in which this portion abuts against the occlusal surface of the tooth. This portion may be provided with depressions and projections corresponding to the projections and depressions of the occlusal surface of the tooth. The above-mentioned portion serves for condensing of the filling material and forming of the occlusal surface of the filling.

The novel features which are considered as characteristic for the present invention are set forth in particular in the appended claims. The invention itself, however, both as to its construction and its method of operation, together with additional objects and advantages thereof, will be best understood from the following description of a specific embodiment when read in connection with the accompanying drawing.

BRIEF DESCRIPTION OF THE DRAWING

The single FIGURE of the drawing is a perspective view showing a matrix device in accordance with the present invention.

DESCRIPTION OF A PREFERRED EMBODIMENT

A device for making fillings in posterior teeth is identified in toto by reference numeral 1. It has a circumferentially complete (uninterrupted) band member 2. The latter is constituted by an elastic or resiliently yieldable material, such as steel, synthetic plastic material and the like. The plastic band member has the advantage in that it does not inflict injuries or cut a gingiva.

The band member 2 has two first portions 2' arranged to surround proximal surfaces of a tooth to be provided with a filling, and two second portions 2" and 2"' arranged to surround a buccal surface and a lingual surface of the tooth, respectively. The first portions 2' are substantially straight, whereas the second portions 2" and 2"' are substantially convex.

Two projections 3 are provided on the portions 2" and 2"'. The projections 3 have concave upper and lower surfaces, so that a dentist can engage each projection by forceps and to put the band member 2 onto the tooth. Of course, one such projection, contrary to two projections, may be formed on the base member 2.

A wedge-shaped tightening member is further provided in the device. When the band member 2 is fitted on the tooth, the wedge-shaped member 4 is inserted inside the band member 2 between the latter and the tooth so that the band member is tightened, abuts against the surfaces of the tooth laterally, and is retained on the tooth so as to form a matrix.

When the filling is to be made near one proximal surface of the tooth (that is in the region of one portion 2' of the band member 2), the wedge-shaped member 4 may be inserted in the region of the portions 2" or/and 2'". When the filling is to be made near the buccal surface (in the region of the portion 2") or near the lingual surface (in the region of the portion 2'") of the tooth, the wedge-shaped member is inserted into the interior of the band member 2 in the opposite regions, that is in the region of the portion 2'" or the portion 2", respectively. Two wedge-shaped members may be provided in the device.

Each of the wedge-shaped members 4 is conical, or more particularly has two transverse dimensions each of which decreases in a direction from above downwardly, in the drawing. Thereby, a linear edge is formed at the lower end of the wedge-shaped member 4. The other end of the wedge-shaped member may be connected to the band member 2. This other end may be connected to the projection 3 of the band member 2, for example by a bendable or elastic filament 5.

The wedge-shaped member 4 may have a projection 6 from which the filament 5 extends. The projection 6 has two concave walls so that it can be grasped by foreceps when the wedge-shaped member 4 is taken by a dentist to be inserted in between the band member 2 and the tooth. The wedge-shaped member 4 are of one piece with the band member 2. However, the wedge-shaped member may be formed by a separate member which are not connected to the band member 2. As can be seen from the drawing, the concave surfaces of the projections 3 and of the projections 6 lie in different planes. The concave surfaces of the projections 6 are lateral surfaces.

One or both portions 2' of the band member 2 surrounding the proximal (mesial and distal) surfaces of the tooth, are provided with a further portion 7 which is bendable or elastically connected with the remainder portion of the band member 2. Each of the portions 7 has projections 7' and/or depressions which correspond to the depressions and projections of the occlusal surface of a regular tooth. In other words, the surface of the portions 7 which faces toward the occlusal surface of the tooth has a profile which is mirror-inverted to the profile of the occlusal surface of the tooth to be provided with a filling. When the material of the filling is first introduced into a cavity of the tooth in a respective region near one of the proximal surfaces of the tooth, the portion 7 is bent toward the remainder portion of the band member 2 or more particularly to the occlusal surface of the tooth so as to abut against the latter from above. The filling material is compressed or condensed, on the one hand. On the other hand, the portion 7 serves as a profiled pumch, so as to form on the occlusal surface of the filling a profile which corresponds to the profile of the occlusal surface of a healthy tooth.

The filament 5 which connects the wedge-shaped member 4 with the band member 2 may be such that it can be torn off or broken off and the wedge-shaped member 4 can be separated from the band member 2. The thus-separated wedge-shaped member 4 may be inserted inside the band member 2 in the region which is spaced from the section to which it has been originally connected.

In order to make easier bending of the portion 7 relative to the band member 2, a section of transition between the former and the latter may be made thinner than the portion 7 and the band member 2. On the other hand, the section of transition between the portion 7 and the band member 2 may have a profile which corresponds to the anatomical shape of the transitional surface between the lateral surface and the occlusal surface of the tooth, or in other words to the anathomical shape of the so-called dental marginal ridge.

It will be understood that each of the elements described above or two or more together, may also find a useful application in other types of constructions differing from the types described above.

While the invention has been illustrated and described as embodied in the above-mentioned arrangement for making filling in posterior teeth, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various modifications and applications without omitting features that, from the standpoint of the prior art, fairly constitutes essential characteristics of the generic or specific aspects of this invention.

What is claimed as new and desired to be protected by Letters Patent is set forth in particular in the appended claims.

1. A device for making fillings in posterior teeth, comprising an elastic band member having a circumferentially complete contour including two first sections arranged to surround proximal surfaces of a tooth and connected by two second sections arranged to surround a buccal surface and a lingual surface of the tooth, respectively; a wedge-shaped tightening member arranged to be inserted between said band member and the tooth inside said band member, so that said band member is tightened and firmly abuts against the tooth and is retained on the latter so as to form a matrix for filling, said wedge-shaped tightening member being of one piece with said band member; and means for connecting said wedge-shaped tightening member with said band member.

2. A matrix device as defined in claim 1, wherein said band member has a portion which is movably connected with the remainder portion of the same and is movable between a first position in which said movable portion abuts against an occlusal surface of the tooth and a second position in which said movable portion is withdrawn from the latter.

3. A matrix device as defined in claim 2, wherein said movable portion is provided with projections and depressions corresponding to depressions and projections of the occlusal surface of the tooth.

4. A matrix device as defined in claim 1, and further comprising at least one projection arranged to be engaged by a tool so as to place said band member onto a tooth.

5. A matrix device as defined in claim 1, wherein said wedge-shaped tightening member has a section provided with a concave wall so that it can be engaged by a tool for insertion into the interior of said band member.

6. A matrix device for making fillings in posterior teeth, comprising an elastic band member having a circumferentially complete contour including two first sections arranged to surround proximal surfaces of a tooth and connected by two second sections arranged to surround a buccal surface and a lingual surface of the tooth, respectively, said band having at least one projection having a concave wall arranged to be engaged by a tool so as to place said band member onto a tooth; and a wedge-shaped tightening member arranged to be inserted between said band member and the tooth inside said band member, so that said band member is tightened and firmly abuts against the tooth and is retained on the latter so as to form a matrix for filling.

7. A matrix device as defined in claim 4, wherein said wedge-shaped tightening member is of one piece with said band member and is connected with said projection of the latter.

8. A matrix device as defined in claim 7, and further comprising an elastic filament connecting said wedge-shaped tightening member to said projection of said band member so as to allow insertion of said wedge-shaped tightening member into the interior of said band member.

* * * * *